US009731151B2

(12) United States Patent
Mores et al.

(10) Patent No.: US 9,731,151 B2
(45) Date of Patent: Aug. 15, 2017

(54) SPRAYABLE SUNSCREEN COMPOSITIONS AND METHODS

(71) Applicant: Honeywell International Inc., Morristown, NJ (US)

(72) Inventors: Lee R. Mores, Jersey City, NJ (US); Mark R. Wheeler, Rockaway, NJ (US); Philip Orawski, Muskegon, MI (US); Bruno Trinquart, Hauts de seine (FR)

(73) Assignee: HONEYWELL INTERNATIONAL INC., Morris Plains, NJ (US)

( * ) Notice: Subject to any disclaimer, the term of this patent is extended or adjusted under 35 U.S.C. 154(b) by 0 days.

(21) Appl. No.: 14/667,112

(22) Filed: Mar. 24, 2015

(65) Prior Publication Data

US 2015/0283052 A1    Oct. 8, 2015

Related U.S. Application Data

(60) Provisional application No. 61/976,530, filed on Apr. 8, 2014.

(51) Int. Cl.

| | | |
|---|---|---|
| *A61K 8/00* | (2006.01) | |
| *A61K 8/18* | (2006.01) | |
| *A61Q 17/04* | (2006.01) | |
| *A61K 8/31* | (2006.01) | |
| *A61K 8/58* | (2006.01) | |
| *A61K 8/81* | (2006.01) | |
| *A61K 8/04* | (2006.01) | |

(52) U.S. Cl.
CPC .............. *A61Q 17/04* (2013.01); *A61K 8/042* (2013.01); *A61K 8/046* (2013.01); *A61K 8/31* (2013.01); *A61K 8/585* (2013.01); *A61K 8/8135* (2013.01); *A61K 2800/48* (2013.01)

(58) Field of Classification Search
CPC .......... A61K 8/046; A61K 8/31; A61K 8/585; A61K 8/8135; A61K 8/062; A61K 8/068; A61K 8/55; A61K 8/896; A61Q 1/02; A61Q 17/00; A61Q 17/005; A61Q 15/00; A61Q 19/00; A61Q 17/04
See application file for complete search history.

(56) References Cited

U.S. PATENT DOCUMENTS

| | | |
|---|---|---|
| 4,200,561 A | 4/1980 | Chang |
| 4,663,157 A | 5/1987 | Brock |
| 4,946,670 A | 8/1990 | Sebag et al. |
| 5,386,003 A | 1/1995 | Greene et al. |
| 5,505,935 A | 4/1996 | Guerrero et al. |
| 6,165,450 A | 12/2000 | Chaudhuri et al. |
| 6,395,269 B1 | 5/2002 | Fuller et al. |
| 6,814,959 B1 | 11/2004 | Muller et al. |
| 6,843,982 B1 | 1/2005 | Arnaud et al. |
| 6,893,646 B2 | 5/2005 | Avalle |
| 7,094,827 B2 | 8/2006 | Fechtenkotter et al. |
| 7,815,924 B2 | 10/2010 | Vonbehren et al. |
| 2003/0026771 A1 | 2/2003 | Hopp |
| 2005/0031847 A1 | 2/2005 | Martens et al. |
| 2005/0048856 A1 | 3/2005 | Hauser et al. |
| 2005/0276763 A1 | 12/2005 | Pfeifer et al. |
| 2006/0024338 A1 | 2/2006 | Hegedus et al. |
| 2006/0051486 A1 | 3/2006 | Dowdell et al. |
| 2006/0116524 A1 | 6/2006 | Bruening et al. |
| 2008/0089913 A1 | 4/2008 | Kallmayer et al. |
| 2009/0035234 A1* | 2/2009 | Cunningham ......... A61K 8/046 424/59 |
| 2009/0068255 A1 | 3/2009 | Yu et al. |
| 2013/0078191 A1* | 3/2013 | Teramoto ................. C09K 3/30 424/45 |
| 2013/0085186 A1 | 4/2013 | Wendel et al. |
| 2014/0086857 A1 | 3/2014 | Blizzard |

FOREIGN PATENT DOCUMENTS

| | | |
|---|---|---|
| DE | 10049041 A1 | 4/2002 |
| GB | 2338650 A | 3/2006 |
| JP | 2008094917 A | 4/2004 |
| WO | 2006048159 A1 | 5/2006 |
| WO | 2012158448 | 11/2012 |

OTHER PUBLICATIONS

Akomeah, Topical Dermatology Drug Delivery: Quo Vadis?, Current Drug Delivery, vol. 7, Issue 4, 2010, pp. 283-296.
Gerhardt et al., Fabrication, Characterisation and Tribological Investigation of Artificial Skin Surface Lipid Films, Current Drug Delivery, vol. 7, Issue 4, 2010, pp. 283-296.
Lee et al., Thixotropic Property in Pharmaceutical Formulations, Journal of Controlled Release, vol. 136, Issue 2, Jun. 5, 2009, pp. 88-98.
Martinez et al., Influence of the Concentration of a Gelling Agent and the Type of Surfactant on the Rheological Characteristics of Oleogels, Il Farmaco 58 (2003) 1289-1294.
International Searching Authority, International Search Report for International Application No. PCT/US2015/022651 dated Jun. 25, 2015.
International Searching Authority, Written Opinion of the International Searching Authority for International Application No. PCT/US2015/022651 dated Jun. 25, 2015.

* cited by examiner

*Primary Examiner* — Nannette Holloman
(74) *Attorney, Agent, or Firm* — Lorenz & Kopf, LLP

(57) ABSTRACT

Disclosed is a sunscreen composition that includes a sunscreen active composition, a volatile, oil phase solvent, and a rheology-modifying ethylene copolymer. The sunscreen composition is in the form of a thixotropic gel. The sunscreen composition may be dispersed to the skin using an aerosol- or non-aerosol-based spray apparatus. The sunscreen composition is provided to prevent ultraviolet radiation from causing damage to skin. Methods for preparing a sunscreen composition are also disclosed.

17 Claims, No Drawings

SPRAYABLE SUNSCREEN COMPOSITIONS AND METHODS

CROSS-REFERENCE TO RELATED APPLICATION

This Application claims the benefit of priority to U.S. Provisional Patent Application Ser. No. 61/976,530, filed on Apr. 8, 2014, the contents of which are incorporated herein by reference in their entirety.

TECHNICAL FIELD

The present disclosure relates to sprayable sunscreen compositions that are suitable for topical application to human skin and hair, and methods for manufacturing and using the same.

BACKGROUND

The damaging effects of sunlight on human skin have long been noted. In general terms, harmful ultra-violet (UV) rays, particularly those originating from sunlight, which penetrate the upper atmosphere and reach the earth's surface can be classified into two types: (i) high energy UV-B rays (290-320 nm wavelength), which are absorbed just above the dermis and are responsible for sunburn and tanning effects; and (ii) low energy UV-A rays (320-400 nm wavelength), which penetrate deeper into the skin (to the dermis and beyond), and which cause damaging effects that are more long term in nature, such as skin ageing.

One method for delivering sunscreen compositions to the skin and hair is in the form of a finely dispersed spray. This form of product delivery offers improved product coverage on the skin or hair and allows easier application on difficult to reach areas. Such a spray is desirably delivered using a spray pump or canister, which may or may not require the use of pressurized containers or special aerosolizing gases. The ability of such spray-driven delivery systems to deliver a product as a finely dispersed spray is dependent upon the viscosity of the composition at the exit port of the pump. As the viscosity of the composition decreases, the spray becomes more dispersed and yields a more desirable delivery. Conversely, as the viscosity increases, the spray becomes less dispersed and more stream-like, yielding a less desirable delivery.

A further consideration is the form that the composition is provided on the skin. It is well known that gel-type compositions exhibit desirable tactile and "feel" properties to the skin. However, gels suitably have a relatively high viscosity, as compared to liquids, and may thus be unsuitable for use in spray sunscreen applications. Accordingly, a spray sunscreen that is dispensed in the form of a finely dispersed spray, while simultaneously having desirable feel properties as applied to the skin, remains elusive.

Thus, there remains a need in the art for sprayable sunscreen composition having desirable viscosity and feel properties. In particular, it would be desirable to provide a sunscreen in gel form, but that is also dispensable as a spray. Still further, other desirable features and characteristics of the inventive subject matter will become apparent from the subsequent detailed description of the inventive subject matter and the appended claims, taken in conjunction with this background of the inventive subject matter.

BRIEF SUMMARY

In one exemplary embodiment, disclosed is a sunscreen composition that includes a sunscreen active composition, a volatile, oil phase solvent, and a rheology-modifying ethylene copolymer. The sunscreen composition is in the form of a thixotropic gel.

In another exemplary embodiment, disclosed is a spray-on sunscreen product that includes a sunscreen composition. The sunscreen composition includes a sunscreen active composition, a volatile, oil phase solvent, and a rheology-modifying ethylene copolymer. The sunscreen composition is in the form of a thixotropic gel. The product further includes a propellant. The sunscreen composition and the propellant are combined within an aerosol spray canister to form the spray-on sunscreen product.

In yet another exemplary embodiment, disclosed is a method for manufacturing a sunscreen composition that includes the steps of solubilizing a sunscreen active component with a volatile, oil phase solvent at a first temperature sufficient to dissolve the sunscreen active component to form a first mixture and adding a rheology-modifying ethylene copolymer at the first temperature to form a second mixture. The method further includes the steps of increasing the temperature of the second mixture to a second temperature that is greater than the first temperature and that is sufficient to melt the rheology-modifying ethylene copolymer and cooling the second mixture to a third temperature that is lower than both the first and second temperatures to form a thixotropic gel.

In yet another exemplary embodiment, disclosed is a method for preventing ultraviolet radiation from causing damage to the skin that includes the steps of topically applying to the skin a sunscreen-effective amount of a sunscreen composition that includes a sunscreen active composition, a volatile, oil phase solvent, and a rheology-modifying ethylene copolymer. The sunscreen composition is in the form of a thixotropic gel.

This brief summary is provided to introduce a selection of concepts in a simplified form that are further described below in the detailed description. This summary is not intended to identify key features or essential features of the claimed subject matter, nor is it intended to be used as an aid in determining the scope of the claimed subject matter.

DETAILED DESCRIPTION

The following detailed description is merely exemplary in nature and is not intended to limit the invention or the application and uses of the invention. As used herein, the word "exemplary" means "serving as an example, instance, or illustration." Thus, any embodiment described herein as "exemplary" is not necessarily to be construed as exemplary or advantageous over other embodiments. All of the embodiments described herein are exemplary embodiments provided to enable persons skilled in the art to make or use the invention and not to limit the scope of the invention which is defined by the claims. Furthermore, there is no intention to be bound by any expressed or implied theory presented in the preceding technical field, background, brief summary, or the following detailed description.

The present disclosure generally provides sunscreen compositions. The sunscreen compositions are provided in the form of a thixotropic gel that exhibits "sheer thinning" properties upon dispensation through a spray canister, pump, valve, or other spray apparatus. When stationary, the composition remains in gel form. However, when moved at a high velocity through the spray apparatus, the composition decreases in viscosity, allowing the composition to be dispensed as a finely dispersed spray.

The sunscreen compositions disclosed herein generally include a sunscreen active composition, a volatile, oil phase solvent, and a rheology-modifying ethylene copolymer. The sunscreen active composition is soluble in the oil phase solvent. The addition of the rheology-modifying ethylene copolymer to the oil phase solvent results in the formation of the thixotropic gel. Greater definition regarding the sunscreen active composition, the volatile, oil phase solvent, and the rheology-modifying ethylene copolymer are provided below, in addition to optional additive compositions that may also be provided in the disclosed sprayable sunscreen composition.

Sunscreen Active Composition

As noted above, the sprayable sunscreen compositions of the present disclosure include at least one sunscreen active composition (hereinafter referred to simply as "sunscreen active"). The sunscreen active may be organic or inorganic, or a combination of both may be used. Suitable sunscreen actives used in the present disclosure include UV absorbers or blockers. UV absorbers may be a UVB or UVA absorber. In some embodiments, the sunscreen active includes more than one organic sunscreen active and/or at least one inorganic sunscreen active. In some embodiments, the sunscreen active includes only a physical blocker sunscreen. At least some of the sunscreen active composition may be oil soluble, for example oil soluble within the oil phase solvent of the presently-described sprayable sunscreen composition.

Any sunscreen active known in the art, or combination thereof, may be used in the compositions described herein. The term "sunscreen active" is intended to include any ultraviolet ray-blocking compounds exhibiting absorption or blockage within the wavelength region between about 290 and 420 nm, or infrared radiation. Sunscreen actives are suitably classified into five groups based upon their chemical structure: amino benzoates; salicylates; cinnamates; benzophenones; and miscellaneous chemicals including menthyl anthralinate and digalloyl trioleate. Inorganic sunscreens may also be used including titanium dioxide, zinc oxide, iron oxide, and polymer particles such as those of polyethylene and polyamides.

Examples of suitable aminobenzoic acids include aminobenzoic acid, its salts, and its derivatives, such as ethyl, isobutyl, and glyceryl esters, p-dimethylaminobenzoic acid, and 4-aminobenzoic acid derivatives, including 4-(dimethylamino)-benzoic acid-2-ethylhexyl ester, 4-(dimethylamino)-benzoic acid-2-octyl ester and 4-(dimethylamino)-benzoic acid amyl ester, and the like.

Examples of suitable cinnamates include cinnamic acid derivatives such as methyl and benzyl esters, α-phenyl cinnamonitrile, butyl cinnamoyl pyruvate, and the like.

Examples of cinnamic acid esters include octinoxate (octyl methoxycinnamate), 4-methoxycinnamic acid propyl ester, 4-methoxycinnamic acid isoamyl ester, and octocrylene (2-ethylhexyl-2-cyano-3,3-diphenylacrylate). Other suitable sunscreen actives include dihydroxycinnamic acid derivatives, trihydroxycinnamic acid derivatives, and the like.

Examples of suitable salicylates include amyl, phenyl, benzyl, menthyl, glyceryl, and dipropylene glycol esters and the like. Specific examples of salicylic acid esters include octisalate (2-ethylhexyl salicylate), salicylic acid-4-isopropylbenzyl ester, and salicylic acid homomethyl ester.

Examples of suitable benzophenones include oxybenzone, sulisobenzone, dioxybenzone, benzoresorcinol, 2,2',4,4'-tetrahydroxybenzophenone, 2,2'-dihydroxy 4,4'-dimethoxybenzophenone, octabenzone, and the like. Suitable derivatives of benzophenone include, for example, 2-hydroxy-4-methoxybenzo-phenone, 2-hydroxy-4-methoxy-4'-methylbenzophenone, 2,2'-dihydroxy-4-methoxy-benzophenone, and the like. Other benzophenone derivatives include sulfonic acid derivatives of benzophenones, for example 2-hydroxy-4-methoxybenzophenone-5-sulfonic acid and salts thereof.

Other suitable sunscreen actives include, for example, 3-benzylidene camphor or 3-benzylidene norcamphor and derivatives thereof, such as 3-(4-methylbenzylidene)-camphor; esters of benzalmalonic acid, such as 4-methoxybenzalmalonic acid di-2-ethylhexyl ester; triazine derivatives such as, for example, 2,4,6-trianilino-(p-carbo-2'-ethyl-1'-hexyloxy)-1,3,5-triazine, and octyl triazone; avobenzone (butyl methoxydibenzoylmethane); ketotricyclo(5.2.1.0)decane derivatives; 2-phenylbenzimidazole-5-sulfonic acid and alkali metal, alkaline earth metal, ammonium, alkylammonium, alkanolammonium and glucammonium salts thereof; sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid, and salts thereof.

Suitable UV-A filters include derivatives of benzoyl methane such as, for example, 1-(4'-tert-butylphenyl)-3-(4'-methoxyphenyl)-propane-1,3-dione, 4-tert-butyl-4'-methoxydibenzoyl methane (Parsol 1789) or 1-phenyl-3-(4'-isopropylphenyl)-propane-1,3-dione. The UV-A and UV-B filters may of course also be used in the form of mixtures.

Besides the oil phase soluble substances mentioned, insoluble light-blocking pigments, i.e. finely dispersed metal oxides or salts, may also be used as part of the sunscreen active composition. Examples of suitable metal oxides are zinc oxide and titanium dioxide and also oxides of iron, zirconium oxide, silicon, manganese, aluminium and cerium and mixtures thereof. Silicates (talcum), barium sulfate and zinc stearate may be used as salts. The particles may have a mean diameter of less than 100 nm, for example between 5 and 50 nm, and more for example between 15 and 30 nm. They may be spherical in shape although ellipsoidal particles or other non-spherical particles may also be used. The pigments may also be surface-treated, i.e. hydrophilicized or hydrophobicized. Suitable examples are coated titanium dioxides, for example Aeroxide $TiO_2$ T805 (Degussa) and Eusolex T2000 (Merck). Preferred hydrophobic coating materials are silicones and, among these, especially trialkoxyoctylsilanes or simethicones. So-called micro- or nanopigments are for example used in sun protection products. Micronized zinc oxide is for example used.

Besides the sunscreen active compounds mentioned above, so-called "secondary sun protection factors" of the antioxidant type may also be used alone or in combination with the previously-described active compounds. Secondary sun protection factors of the antioxidant type interrupt the photochemical reaction chain which is initiated when UV rays penetrate into the skin. Suitable examples are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (for example pmole to .mu. mole/kg), also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxybutyrophenone, uric acid and derivatives thereof, mannose and derivatives thereof, Superoxide-Dismutase, zinc and derivatives thereof (for example ZnO, $ZnSO_4$), selenium and derivatives thereof (for example selenium methionine), stilbenes and derivatives thereof (for example stilbene oxide, trans-stilbene oxide) and derivatives of these active substances suitable for the purposes of the disclosure (salts, esters, ethers, sugars, nucleotides, nucleosides, peptides and lipids).

In exemplary embodiments, the sunscreen actives are FDA approved or approved for use in the European Union. Examples of suitable FDA approved sunscreen actives are described in the Final Over-the-Counter Drug Products Monograph on Sunscreens (Federal Register, 1999: 64:27666-27693), herein incorporated by reference. It should be understood that the specific sunscreen actives and amounts thereof that are approved for use in the United States or European Union are subject to periodic change. As such, the specific examples and amounts set forth herein are not intended to be limiting.

For example, for a product marketed in the United States, exemplary cosmetically-acceptable sunscreen actives and concentrations (reported as a percentage by total weight of the composition) may include aminobenzoic acid (i.e., para-aminobenzoic acid or PABA) in amounts up to 15%; avobenzone (i.e., butyl methoxy dibenzoylmethane) in amounts of up to 3.0%; cinoxate(2-ethoxyethyl p-methoxycinnamate) in amounts up to 3.0%; dioxybenzone (i.e., benzophenone-8) in amounts up to 3.0%; homosalate in amounts up to 15.0%; menthyl anthranilate in amounts up to 5.0%; octocrylene (i.e., 2-ethylhexyl-2-cyano-3,3 diphenylacrylate) in amounts up to 10%; octinoxate (i.e., octyl methoxycinnamate) in amounts up to 7.5%; octisalate (i.e., octyl salicylate or 2-ethylhexyl salicylate) in amounts up to 5.0%; oxybenzone (i.e., benzophenone-3) in amounts up to 6.0%; padimate O (i.e., octyl dimethyl PABA) in amounts up to 8.0%; phenylbenzimidazole sulfonic acid in amounts up to 4.0%; sulisobenzone in amounts up to 10%; titanium dioxide in amounts up to 25.0%; trolamine salicylate in amounts up to 12.0%; and zinc oxide in amounts up to 25.0%. Combinations of these actives may also be used.

For a product marketed in the European Union, exemplary sunscreen actives and concentrations (reported as a percentage by total weight of the composition) may include: PABA in amounts up to 5.0%, camphor benzalkonium methosulfate in amounts up to 6.0%, homosalate in amounts up to 10.0%, oxybenzone in amounts up to 10.0%, phenylbenzimidazole sulfonic acid in amounts up to 8.0%, terephthalidene dicamphor sulfonic acid in amounts up to 10.0%, avobenzone in amounts up to 5.0%, benzylidene camphor sulfonic acid in amounts up to 6.0%, octocrylene in amounts up to 10.0%, polyacrylamidomethyl benzylidene camphor in amounts up to 6.0%, octinoxate in amounts up to 10.0%, PEG-25 PABA in amounts up to 10.0%, isoamyl p-methoxycinnamate in amounts up to 10.0%, ethylhexyl triazone in amounts up to 5.0%, drometrizole trielloxane in amounts up to 15.0%, diethylhexyl butamido triazone in amounts up to 10.0%, 4-methylbenzylidene camphor in amounts up to 4.0%, 3-benzylidene camphor in amounts up to 2.0%, octisalate in amounts up to 5.0%, ethylhexyl dimethyl PABA in amounts up to 8.0%, sulisobenzone in amounts up to 5.0%, methylene bis-benztriazolyl tetramethylbutylphenol in amounts up to 10.0%, disodium phenyl dibenzimidazole tetrasulfonate in amounts up to 10.0%, bis-ethylhexyloxyphenol methoxyphenol triazine in amounts up to 10.0%, methylene bisbenzotriazolyl tetramethylbutylphenol in amounts up to 10.0%, and bisethylhexyloxyphenol methoxyphenyl triazine in amounts up to 10.0%. Combinations of these actives may also be used. It will be appreciated by those of skill in the art that the various sunscreen actives may be added to the composition all at once, or in groups, or separately.

The total amount of sunscreen active present in the sprayable sunscreen compositions of the present disclosure may vary depending on the target post-immersion SPF (after exposure to water) of the composition. For example, the sunscreen compositions of the present disclosure may have a static SPF of from about 15 to about 90, and more suitably from about 30 to about 60, and a post-immersion SPF of at least about 25, more for example at least about 40, and more for example at least about 50. As such, the compositions may for example include a total amount of sunscreen active sufficient to achieve these target SPF ratings.

For example, however, the composition may comprise not more than about 40% (by total weight of the composition) of sunscreen actives, such as not more than about 35%. Inclusion of sunscreen actives into the compositions in amounts of about 40% (by total weight of the composition) may for example achieve a static SPF of at least about 50, and a post-immersion SPF of at least about 50. It is to be understood that static and post-immersion SPF ratings below 40 may also be achieved by lowering the amount of sunscreen actives included in the composition.

Carriers

As initially noted, the sprayable sunscreen compositions of the present disclosure suitablely include a carrier provided in the form of a thixotropic gel. The carrier should be cosmetically and/or pharmaceutically acceptable, which reflects that the carrier is suitable for topical application onto the skin, has good aesthetic properties, is compatible with the other components of the composition, and may not cause any untoward safety or toxicity concerns. As used herein, the phrase "suitable for topical application onto human skin" reflects that the carrier does not damage or negatively affect the aesthetics of or cause irritation to human skin. The thixotropic gel carrier suitablely constitutes from about 10% to about 90% by weight, for example from about 40% to about 70% by weight, more for example from about 50% to about 60% by weight, of the composition. Upon application of the composition to the skin (via spraying), the carrier evaporates and leaves behind a thin film comprising the active ingredients and any other composition components deposited on the skin. The film, containing the sunscreen actives, remains on the skin and protects the skin from ultraviolet radiation and damage resulting therefrom. Since the sunscreen compositions are for example formulated for spray on application, it is generally preferable for the carrier to include components that are capable of evaporating upon application of the composition to the skin. Examples of suitable materials for use as part of the thixotropic gel carriers include volatile, oil phase solvents. Examples of suitable volatile, oil phase solvents include ethyl trisiloxane, isododecane, cyclopentasiloxane, and mixtures thereof.

Rheology Modifying Copolumer

As initially noted above, the thixotropic gel carrier of the presently disclosed sprayable sunscreen compositions includes a rheology modifying ethylene copolymer, which, when added to the above-described oil-phase solvent, forms a compatible, stable, thixotropic gel. As used herein, the term "compatible" is used herein to mean that at room temperature between 15°-25° C., the gel does not separate into visibly distinct phases or become visibly grainy because of the gellant crystallizing out in microscopic particles. Compatibility may be determined by forming a mixture of gel components at elevated temperatures, such as 70°-100° C., and cooling the mixture to room temperature with stirring. Incompatible mixtures may show droplets or grains when pressed between two microscope slides or exhibit excessive cloudiness compared to compatible gels. Another measure of compatibility is to heat together all the components of the gel to a given temperature (dependent on composition), and then determine whether a clear, haze-free liquid is observed.

With respect to the thixotropic gel carrier, the term "stable" is used herein to mean that the gel does not readily flow in the absence of shear, such as when a spray container of gel is turned on its side. "Stable" is also meant to include a gel remaining compatible throughout the temperature range of 10° to 50° C. (and for example over a broader temperature range). Gels with insufficient amounts of the present-described rheology-modifying ethylene copolymers may separate or flow, especially at temperatures of 30°-50° C., since the quantity of ethylene copolymer microcrystals may be insufficient to maintain the gel structure. If, as is normally the case, the ethylene copolymer particles are denser than the oil-phase solvent (or any co-solvent that may be present), then a liquid layer may form, with time on top of the gel evidencing instability of the gel and resulting in a "too thin" application.

The term "thixotropic" is broadly used herein in its normal meaning of spreading or flowing with stress, but remaining stable in the absence of stress. More fully, in accordance with the present disclosure, the term thixotropic refers to a composition wherein the extent of thinning is dependent upon the shear applied and the time for which the shear is applied, and wherein the time taken for the viscosity of the gel to rebuild its original viscosity is fixed dependent upon the original gel or mixture. With regard to the presently disclosed thixotropic sunscreen compositions, the rapid build-up of viscosity after passing through the spray valve, nozzle, or other spray apparatus helps minimize the overspray and contributes to better film formation on the skin. Furthermore, as applied to the present disclosure, the flowing stress may be applied as a result of the gel passing at a relatively high rate of speed through a spray valve, nozzle, or other spray apparatus.

In the composition of the thixotropic gel, as initially noted above, the oil phase solvent may include any volatile oil phase constituent or mixture of constituents, with ethyl trisiloxane, isododecane, and cyclopentasiloxane (and mixtures thereof) being exemplary. The gelling agent of the disclosure may be any of a variety of ethylene copolymers. Suitable copolymers and methods for their preparation are described in U.S. Pat. No. 3,658,741 to Knutson et al. (issued Apr. 25, 1972) and U.S. Pat. No. 3,909,280 to Seven et al. (issued Sep. 30, 1975), the contents of which are herein incorporated by reference in their entirety. Ethylene copolymers satisfying the present criteria are also known and commercially available.

The ethylene copolymer may have a number average molecular weight, as generally understood in the polyethylene art, between about 500 and about 10,000 with those between about 1000 and about 5000 being exemplary. In a particular, embodiment, a number average molecular weight between about 2000 and about 4000 is used, with certain exemplary embodiments having average molecular weights about 2000, about 3000, about 3200, and about 3500.

Several unsaturated acid monomers (acrylic, methacrylic and ethacrylic acids) may be incorporated into the copolymer during polymerization, as may vinyl esters (vinyl acetate, vinyl formate and vinyl propionate). Esterified acrylic acid monomers are produced by polymerizing acrylic acid with ethylene and the partially or completely esterifying the copolymer product with an alcohol such as methanol, ethanol, propanol, isopropanol, butanol, isobutanol, t-butanol or higher alcohols up to about 22 carbons. It is also exemplary that such acid copolymers be only partially esterified, such as down to an acid number of about 5-10.

The ethylene copolymer gellant need not be the sole gellant or sole oil phase gellant employed. Thus, beeswax, carnauba wax or other organically derived waxes of the type conventionally employed in thixotropic gels may be used in conjunction with the ethylene copolymer. In one particular embodiment, especially in gels which are relatively thin by virtue of a low proportion of gellant (under 10% of the oil phase), such other waxes may be used in relatively minor proportions such as less than 50% by weight of the copolymer gellant.

The proportion of ethylene compared to comonomer in the copolymer is not critical, although a broad range of about 40-90 mole % ethylene is suitable. In a particular embodiment, at least about 1-50 mole % of the copolymer will be one or more comonomers. The several esters named as comonomers are for example present at between about 1 and 50 mole %, with about 5 to about 30 mole % being exemplary and between about 5 and about 20 mole % being most exemplary. The several unsaturated acids named as comonomers are for example present in proportions giving an acid number (in mg KOH/g) between about 30 and about 150, with between about 30 and 80 being exemplary.

In one exemplary embodiment, the rheology-modifying ethylene copolymer is an ethylene/vinyl acetate copolymer. A particularly exemplary copolymer is marketed under the tradename Asensa CL 300, available from Honeywell International Inc. of Morristown, N.J., USA.

As a percentage of the overall sprayable sunscreen composition, the rheology-modifying ethylene copolymer may be present in an amount of from about 5% to about 20%, for example of from about 7% to about 15%. Stated alternatively, the ratio of the oil phase solvent to the rheology-modifying ethylene copolymer may be from about 10:1 to about 3:1, for example from about 8:1 to about 4:1.

The thixotropic sunscreen compositions are for example prepared by heating and mixing the ingredients together under a homogeneous solution results. Solution temperature, depending on composition can be in the range of 70°-130° C. The gels are then cooled fast with agitation. This forces the polyethylene to crystallize out in very fine particle size. If the gel favors large crystal growth, fast cooling keeps the crystals from growing further and the gels are generally thixotropic, opaque, and stable. Slow cooling of these gels could normally result in a coarse, unstable gel. With quick cooling, these crystals are so small in particle size that when the gel is pressed between two glass plates in a thin film, they are transparent and therefore no longer reflect light.

For example, in the preparation of the sprayable sunscreen composition, the sunscreen active component(s) are first solubilized within the volatile, oil phase solvent(s) (and any cosolvent(s)), at a temperature sufficient to dissolve the sunscreen active, for example from about 40° C. to about 55° C. The rheology-modifying ethylene copolymer is then added to the mixture, and the mixture is heated to a temperature sufficient to melt the copolymer, for example a temperature of about 85° C. to about 95° C. The composition is then quickly reduced to room temperature to form the thixotropic gel composition.

Optional Components

Optionally, the sunscreen compositions of the present disclosure may further include a component that provides a film barrier, suitablely a hydrophobic layer that serves to maintain the sunscreen actives on the skin after immersion in water, such as a waterproofing agent or other film former. For example, the waterproofing agents used herein are acrylic co-polymers. Acrylic co-polymers may be included in the sunscreen compositions in amounts of from about 0.5% (by total weight of the composition) to about 5.0% (by total weight of the composition), for example from about 1.0% (by total weight of the composition) to about 5.0% (by total weight of the composition), and for example from about 2.0% (by total weight of the composition) to about 4.0% (by total weight of the composition). Other suitable waterproofing agents and film formers are well-known in the art and include, without limitation, petrolatum, emollient esters, lanolin derivatives (e.g., acetylated lanolins), superfatted oils, cyclomethicone, cyclopentasiloxane, dimethicone, natural and synthetic oils, fatty acids, fatty alcohols, waxes, and the like, and mixtures thereof.

In addition, many emollients may also exhibit a film forming function in that they provide a water-resistant barrier on the skin. Thus, the sunscreen compositions of the present disclosure may optionally include an emollient. A particularly exemplary emollient is butyloctyl salicylate. Emollients such as butyloctyl salicylate may be included in the composition in amounts for example not more than about 10.0% (by total weight of the composition), more for example in amounts of from about 0.1% (by total weight of the composition) to about 10.0% (by total weight of the composition), for example from about 1.0% (by total weight of the composition) to about 8.0% (by total weight of the composition), and more for example about 3.5% (by total weight of the composition) to about 7.0% (by total weight of the composition).

Other emollients suitable for inclusion in the sunscreen compositions of the present disclosure may include water-insoluble emollients that include fatty acids such as oleic and stearic; fatty alcohols such as cetyl, and hexadecyl; esters such as diisopropyl adipate, benzoic acid esters of $C_1$-$C_{15}$ alcohols, and isononyl isononanoate; alkanes such as mineral oil; ethers such as polyoxypropylene butyl ethers and polyoxypropylene cetyl ethers; and natural and synthetic oils; and mixtures thereof.

A preservative, such as an antimicrobial preservative, can also be optionally added to the sunscreen compositions as described herein. An antimicrobial preservative is a compound or substance that destroys, prevents, or inhibits the multiplication/growth of microorganisms in the sunscreen composition and may offer some protection from oxidation of the sunscreen composition. Suitable preservatives include, for example, the lower alkyl esters of para-hydroxybenzoates such as methylparaben, propylparaben, isobutylparaben, and mixtures thereof, benzyl alcohol, DMDM Hydantoin, and benzoic acid, and mixtures thereof.

Another optional ingredient that can be added to the sunscreen compositions described herein is an antioxidant, which is a natural or synthetic substance added to the sunscreen composition to protect it from decay or deterioration due to the reaction with oxygen in the air. Antioxidants prevent deterioration which may lead to the generation of rancidity and non-enzymatic browning reaction products. Suitable antioxidants include, for example, propyl, octyl and dodecyl esters of gallic acid, butylated hydroxyanisole, butylated hydroxytoluene, nordihydroguaiaretic acid, vitamin E, vitamin E acetate, vitamin C, lipoic acid, ubiquinone, Apple Green Tea, Arnica Special, Avocado GW, Bell Pepper Fruit, Black Currant B, Black Currant Green Tea, Blueberry Fruit, Cabbage Rose Extract, Camellia sinensis, Canadian Willowherb, Carrot Root, Camellia Oleifera Extract, Common thyme, Cranberry Green Tea, Echinacea Dry Aqueous Extract, Fennel Fruit, Ginkgo Biloba, Glycine Max (soybean seed), Goldenseal, Grapefruit, Grape Seed Extract and constituents thereof (proanthocyanidins), Grapefruit Green Tea, Green Tea, catechin constituents of Green Tea that include epigallocatechin gallate, epicathechin gallate, Green Tea Extra, Green Tea HS, Lime Blossom, Orange Green Tea, Rosemary Plant, Sea Parsley, St. John's Wort W/S, Strawberry Fruit, Tomato Root, Turkish Oregano, Wheat Seed, White Mistle Toe, White Tea, Yarrow, Yucca 70, Yucca Extract Powder, and combinations thereof.

Fragrances can also be added to the sunscreen compositions described herein. Fragrances are aromatic compounds which can impart an aesthetically pleasing aroma to the sunscreen composition. Suitable fragrances include, for example, aromatic materials extracted from botanical sources such as rose petals, gardenia blossoms, and jasmine flowers which can be used alone or in any combination to create essential oils. Additionally, alcoholic extracts may be prepared for fragrances. The fragrance may be included in the composition in amounts of from about 0.1% (by total weight of the composition) to about 2.0% (by total weight of the composition), and for example of from about 0.5% (by total weight of the composition) to about 1.0% (by total weight of the composition).

Another ingredient that may optionally be added to the sunscreen composition in some embodiments of the present disclosure include humectants. A humectant is a moistening agent that promotes retention of water due to its hydroscopic properties, and moisturizes the skin. One or more humectants may be introduced into the sunscreen composition in an amount of from about 0.1% (by total weight of the composition) to about 10.0% (by total weight of the composition). Suitable humectants for inclusion in the sunscreen compositions described herein include, for example, any known oil-soluble humectants.

Additional optional ingredients that can be incorporated into the sunscreen compositions include vitamins, skin protectants, powders, skin conditioners, botanicals, natural extracts, alpha hydroxy acids, moisturizers, aesthetic modifiers, light reflectants, fats and oils, lipids, fatty alcohols, fatty acids, colorants, pigments, optical brighteners, essential oils, and mixtures thereof.

Suitable spray compositions are well known in the art and include conventional, non-aerosol pump sprays, i.e., "atomizers," aerosol containers or cans having propellant, as described above, and also pump aerosol containers utilizing compressed air as the propellant. With regarding to the optional use of propellants, suitably, the propellant is a liquefied propellant under pressure. For example, the liquefied propellant may be responsible for and/or produces a fine, even and consistent spray, particularly on being discharged from the container. In one embodiment, the propellant may convert into a gaseous phase on leaving the container at the point of discharge from the container. As such, the propellant aids in distribution of the sunscreen agent or agents in the mist or spray.

For example, the propellant may be a gas or mixture of gases, or a compressed gas or a mixture of compressed gases. For example, the gas may be air or an air containing gas. In one embodiment, the propellant may be a volatile material, such as a material having a low boiling point that causes it to evaporate quickly. The propellant may have a high volatility, particularly at room temperatures. The boiling points of the propellants vary from about −500° C. to about 500° C. In an exemplary embodiment, low global warming potential propellants may be used, such as, for example, HFO-1234ze, which is an unsaturated fluorocarbon (trans-1,3,3,3-tetrafluoroprop-1-ene) available from Honeywell International, Inc. of Morristown, N.J., USA. Other suitable propellants include dimethylether, 1,2-difluoroethane, propane, n-butane, isobutene, and mixtures thereof. The propellant may be used in an aerosol spray canister in a weight ratio, with respect to the sunscreen composition of about 3:1 to about 1:3, with about 1:1 being exemplary.

The spray may in the form of a fine particle size or fine droplet size mist, fog, aerosol, spray or the like. For example, the spray may have a particle size or droplet size of from about 0.1 micron to about 5000 micron, for example from about 0.2 micron to about 1000 micron, more for example from about 1.0 micron to about 500 micron. The spray or mist delivers a fine even coverage of a film of the sunscreen composition to skin surfaces.

ILLUSTRATIVE EXAMPLE

The present disclosure is now illustrated by the following non-limiting example. It should be noted that various changes and modifications can be applied to the following example and processes without departing from the scope of this disclosure, which is defined in the appended claims. Therefore, it should be noted that the following example should be interpreted as illustrative only and not limiting in any sense.

A sprayable sunscreen composition was prepared according to the following Example. The sunscreen active ingredients and several optional humectant/emollient ingredients were combined into a Phase A, in the following percentages, based on the overall sunscreen composition.

Phase A:

| | |
|---|---|
| Butyloctyl Salicylate | 5.00 |
| Octinoxate | 7.50 |
| Octocrylene | 2.75 |
| Avobenzone | 3.00 |
| Homosalate | 10.00 |
| Octisalate | 5.00 |
| Polyester-8 | 3.00 |

-continued

| | |
|---|---|
| Neopentyl Glycol Diheptanoate | 30.75 |
| Dicapryl Ether | 3.00 |

Phase A was then heated to about 50° C. to about 55° C. to dissolve the ingredients. Phase A was then cooled to about 40° C. to about 45° C. The volatile, oil phase solvents were combined into a Phase B, in the following percentages, based on the overall sunscreen composition.

Phase B:

| | |
|---|---|
| Ethyl Trisiloxane | 9.25 |
| Isododecane | 8.50 |
| Cyclopentasiloxane | 4.25 |

Phase B was then added to Phase A at the above-noted temperature of about 40° C. to about 45° C. The mixture was then stirred until uniform.

Phase C:

| | |
|---|---|
| Ethylene/VA Copolymer | 8.00 |

Phase C was then combined with the Phases A and B mixture, and then the resulting mixture was heated to a temperature of about 90° C. to about 95° C. to melt the Phase C. The resulting mixture was then stirred until uniform. The resulting mixture was then quickly cooled to about room temperature to form a thixotropic gel, sprayable sunscreen composition in accordance with the present disclosure. The sprayable sunscreen composition was added to an aerosol canister and a HFO-1234ze propellant was also added thereto in a weight ratio of about 1:1.

As such, described herein are thixotropic gel sunscreen compositions suitable for use in spray-on applications. The sunscreen compositions are desirable sprayable for uniform application to the skin, while desirable retaining the feel qualities of a gel composition.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope as set forth in the appended claims and their legal equivalents.

What is claimed is:

1. A sunscreen composition comprising:
    a sunscreen active composition;
    a volatile, oil phase solvent; and
    a rheology-modifying ethylene copolymer,
    wherein the sunscreen composition is in the form of a thixotropic, stable gel;
    wherein the thixotropic, stable gel does not readily flow in the absence of shear applied to the gel.

2. The sunscreen composition of claim 1, wherein the sunscreen active composition is selected from the group consisting of: butyloctyl salicylate, octinoxate, octocrylene, avobenzone, homosalate, octisalate, and mixtures thereof.

3. The sunscreen composition of claim 1, wherein the sunscreen active composition is provided in an amount, by weight of the overall sunscreen composition, of not more than about 40%.

4. The sunscreen composition of claim 1, wherein the volatile, oil phase solvent is selected from the group consisting of: ethyl trisiloxane, isododecane, cyclopentasiloxane, and mixtures thereof.

5. The sunscreen composition of claim 1, wherein the volatile, oil phase solvent is provided in an amount, by weight of the overall sunscreen composition, of from about 40% to about 70%.

6. The sunscreen composition of claim 1, wherein the rheology-modifying ethylene copolymer is selected from the group consisting of: ethylene/vinyl acetate copolymers.

7. The sunscreen composition of claim 1, wherein the rheology-modifying ethylene copolymer is provided in an amount, by weight of the overall sunscreen composition, of from about 5% to about 20%.

8. A spray-on sunscreen product comprising:
a sunscreen composition, wherein the sunscreen composition comprises a sunscreen active composition, a volatile, oil phase solvent, and a rheology-modifying ethylene copolymer, and wherein the sunscreen composition is in the form of a thixotropic, stable gel; and
a propellant,
wherein the sunscreen composition and the propellant are combined within an aerosol spray canister to form the spray-on sunscreen product;
wherein the thixotropic, stable gel does not readily flow in the absence of shear applied to the gel.

9. The spray-on sunscreen product of claim 8, wherein the propellant comprises (trans-1,3,3,3-tetrafluoroprop-1-ene).

10. The spray-on sunscreen product of claim 8, wherein the propellant and the sunscreen composition are provided in a weight ratio of about 1:1.

11. A method for manufacturing a sunscreen composition comprising the steps of:
solubilizing a sunscreen active component with a volatile, oil phase solvent at a first temperature sufficient to dissolve the sunscreen active component to form a first mixture;
adding a rheology-modifying ethylene copolymer at the first temperature to form a second mixture;
increasing the temperature of the second mixture to a second temperature that is greater than the first temperature and that is sufficient to melt the rheology-modifying ethylene copolymer; and
cooling the second mixture to a third temperature that is lower than both the first and second temperatures to form a thixotropic, stable gel;
wherein the thixotropic, stable gel does not readily flow in the absence of shear applied to the gel.

12. The method of claim 11, wherein solubilizing at the first temperature comprises solubilizing at a temperature of about 40° C. to about 55° C.

13. The method of claim 11, wherein increasing to the second temperature comprises increasing to a temperature of about 85° C. to about 95° C.

14. The method of claim 11, wherein cooling to the third temperature comprises cooling to a temperature of about 15° C. to about 25° C.

15. The method of claim 11, wherein forming the thixotropic gel comprises forming a compatible, stable, thixotropic gel.

16. The spray-on sunscreen product of claim 8, wherein the rheology-modifying ethylene copolymer is provided in an amount, by weight of the overall sunscreen composition, of from 7% to 15%.

17. The spray-on sunscreen product of claim 8, wherein a ratio of the volatile, oil phase solvent to the rheology-modifying ethylene copolymer is from 8:1 to 4:1.

* * * * *